United States Patent

Widlund

Patent Number: 5,454,804
Date of Patent: Oct. 3, 1995

[54] SANITARY NAPKIN OR AN INCONTINENCE GUARD HAVING FLEXIBLE SIDE-FLAPS

[75] Inventor: Urban Widlund, Mölnlycke, Sweden

[73] Assignee: Molnlycke AB, Goteborg, Sweden

[21] Appl. No.: 39,325

[22] PCT Filed: Oct. 31, 1991

[86] PCT No.: PCT/SE91/00736
§ 371 Date: Apr. 23, 1993
§ 102(e) Date: Apr. 23, 1993

[87] PCT Pub. No.: WO92/07537
PCT Pub. Date: May 14, 1992

[30] Foreign Application Priority Data

Nov. 1, 1990 [SE] Sweden ................................. 9003489

[51] Int. Cl.[6] ........................... A61F 13/15; A61F 13/20
[52] U.S. Cl. ................. 604/389; 604/358; 604/385.1; 604/386; 604/387; 604/390
[58] Field of Search ................................ 604/358, 372, 604/385.1, 386, 387, 389, 390

[56] References Cited

U.S. PATENT DOCUMENTS

| | | |
|---|---|---|
| 4,285,343 | 8/1981 | McNair . |
| 4,608,047 | 8/1986 | Mattingly . |
| 4,701,178 | 10/1987 | Glaug et al. . |
| 4,950,264 | 8/1990 | Osborn, III . |
| 5,154,715 | 10/1992 | Van Iten ................................. 604/386 |
| 5,389,094 | 2/1995 | Lavash et al. ......................... 604/358 |

FOREIGN PATENT DOCUMENTS

32764/89 12/1989 Australia .

Primary Examiner—Randall L. Green
Assistant Examiner—P. Zuttarelli
Attorney, Agent, or Firm—Young & Thompson

[57] ABSTRACT

The invention relates to an absorbent article, such as a sanitary napkin or an incontinence guard intended to be worn in the crotch part of a pair of underpants (9), and comprising an elongated absorbent pad (3) which is enclosed in a casing (1, 2) and which has attached to both long side edges (6, 7) flexible flaps (4, 5) which are intended to be folded around the leg edges (10, 11) of the underpants (9) in use, so as to prevent soiling of the underpants. An inventive article is mainly characterized in that each flap (4, 5) has an edge part which coincides generally with a corresponding edge part on the article casing (1, 2), and in that the flaps (4, 5) and the casing (1, 2) are mutually joined within the mutually coincidental edge parts (12, 13), with the flaps (4, 5) extending inwardly over the absorbent pad (3).

6 Claims, 2 Drawing Sheets

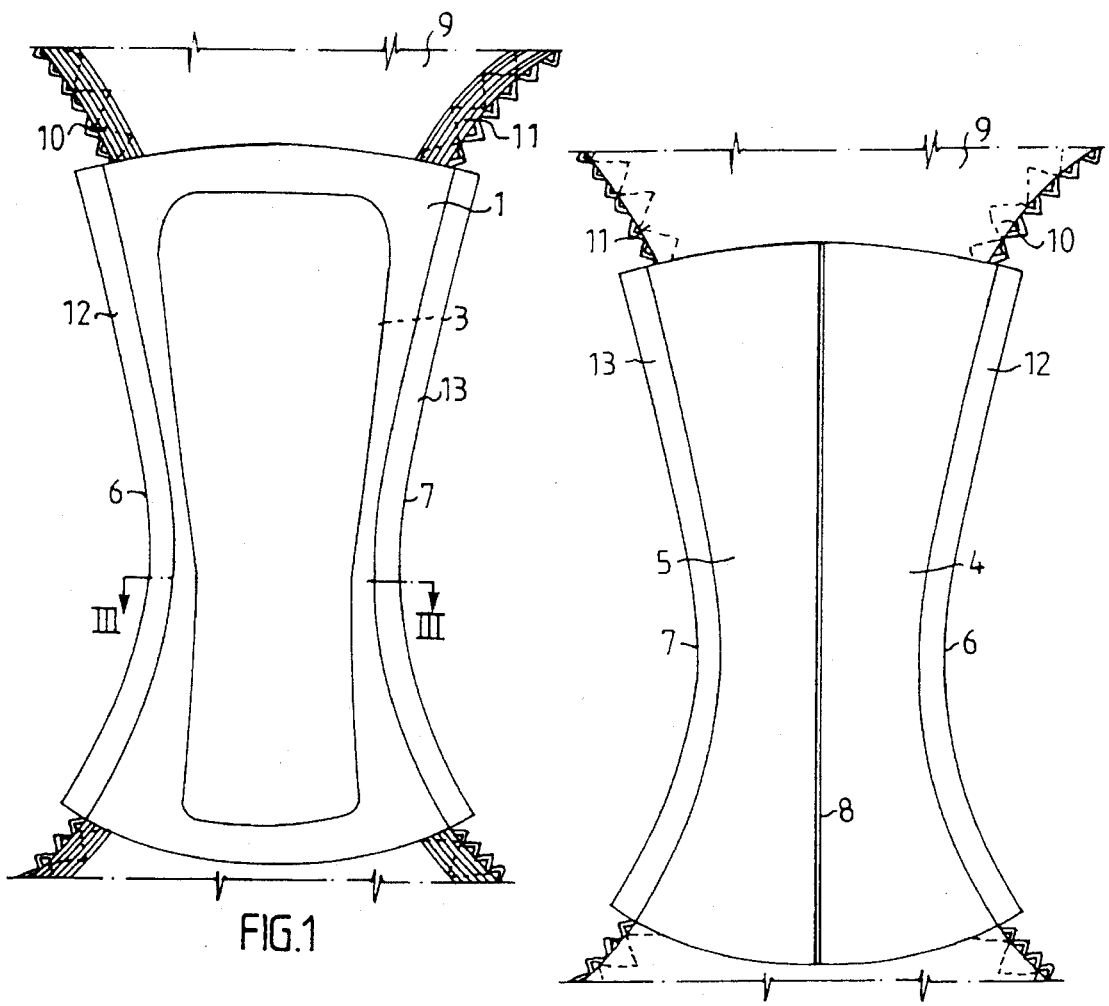
FIG.1
FIG.2
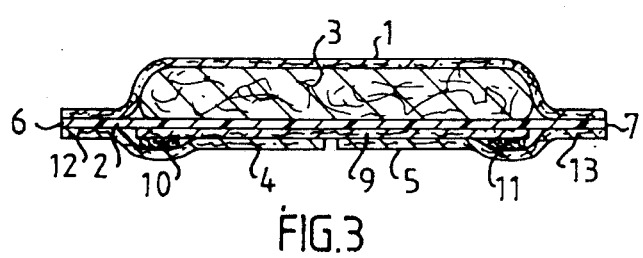
FIG.3

SANITARY NAPKIN OR AN INCONTINENCE GUARD HAVING FLEXIBLE SIDE-FLAPS

FIELD OF THE INVENTION

The present invention relates to an absorbent article, such as a sanitary napkin or an incontinence guard, intended to be worn in the crotch part of a pair of underpants and including an elongated absorbent pad enclosed in a casing, and flexible flaps which are attached to respective long edges of said pad, said flaps being formed of separate material pieces and intended to be folded around the leg edges of the underpants in use, so as to protect the underpants against soiling.

BACKGROUND OF THE INVENTION

Articles of this kind are intended to be worn by menstruating women or by persons who suffer from relatively light incontinence, and who require the articles to afford protection against leakage but still be unnoticeable when worn beneath conventional clothing. Since the amount of fluid discharged with menstruation and with light incontinence is relatively small, the articles can be designed in a manner which enables them to be accommodated essentially fully in the crotch region, between the wearer's thighs. The requirement that such articles shall be discrete when worn is satisfied almost to the full by said articles.

However, it has been found difficult to produce articles of this kind which are sufficiently proof against leakage. The main reason for this is that, when worn, the articles are highly deformed by the forces that are generated as the wearer moves. The greatest deformation normally occurs within that part of the article which, in use, is located in the narrowest space between the wearer's thighs. Unfortunately, this part of the article is also the part which is intended to receive the discharged body fluid first and to absorb said fluid. As a result of this pronounced deformation of the article, the surface area of the article available for direct absorption is, of course, greatly reduced. This increases the risk of body fluid leaking past the side edges of the article and soiling the user's underpants.

A number of different methods of reducing the risk of lateral leakage have been proposed. For example, SE 455 668, U.S. Pat. No. 4,285,343, EP 130 848, EP 134 086 and U.S. Pat. No. 4,608,047 teach sanitary napkins which are provided with flexible flaps, or wings, that protrude outwardly from the absorbent pad. These flaps are intended to be folded around the edges of the leg openings of the wearer's underpants or like garment and fastened to the outside of said underpants when fitting the napkin for use. The flaps thereby form a protective guard against the lateral leakage of body fluids and soiling of the underpants.

These earlier known, so-called winged sanitary napkins are encumbered with several drawbacks, however. For example, sanitary napkins of this kind are found difficult to manipulate by many users, mainly because of the difficulty found in folding and shaping the wings around the curved edges of the leg openings of a pair of underpants or like garment. This problem is particularly manifest in the case of sanitary napkins whose wings or side-flaps have large extensions in the longitudinal direction of the article, since it is necessary to fold the wings around a relatively large part of the leg edges of the underpants. Wings which extend along only a small part of respective side edges of the napkin can be folded around the edges of the leg openings more easily, but these flaps, naturally, provide much poorer protection against leakage than the large flaps.

The known winged sanitary napkins are normally secured to the underpants of the wearer by means of pressure-sensitive adhesive provided on the wings, in the form of adhesive beads, strings or the like along the longitudinal center line of the napkin, on that side of the napkin which is distal from the wearer in use. Prior to use, the pressure-sensitive adhesive is covered with a protective release strip, which is removed when the binder is to be secured to the wearer's underpants.

When securing winged sanitary napkins of this kind to the wearer's underpants, the work involved in removing the various protective layers and in folding and securing the wings is quite comprehensive. Furthermore, the work involved must be carried out in the correct sequence in order to avoid prematurely exposed adhesive surfaces from fastening to the underpants in the wrong places and therewith making it difficult to position the napkin correctly.

The known winged sanitary napkins normally comprise an absorbent pad which is enclosed by two casing sheets. These sheets extend beyond the side edges of the absorbent pad, to form the wings of the napkin. This, of course, is a simple construction which affords certain manufacturing advantages. However, a great deal of material is wasted when cutting such napkins to shape, which is obviously a disadvantage. Furthermore, it is necessary to fold the wings together so that the napkins can be packaged, which complicates the manufacturing process.

Furthermore, the fact that the napkin casing material merges directly with the wings is disadvantageous from a purely functional aspect, since body fluid can then be transported from the absorbent pad to the wings, causing leakage.

The present invention provides an article of the aforedescribed kind which avoids the drawbacks associated with known articles of this kind.

SUMMARY OF THE INVENTION

An article constructed in accordance with the invention is mainly characterized in that each flap has an edge part which coincides generally with a corresponding edge part on the article casing; and in that the flaps and the casing are mutually Joined within the mutually coincident edge parts, with the flaps facing each other with their free edge parts extending inwardly over the absorbent pad on the side of the casing remote from the wearer when the article is in use.

According to one embodiment of the invention, the longitudinally extending side edges have a concave curvature, thereby imparting to the article a shape which conforms generally with the shape of the crotch of a pair of underpants or like garment.

According to another embodiment, the flaps extend along the whole length of the side edges of the article.

According to another embodiment, the casing includes a liquid-permeable sheet on that side of the object which faces the user in use, and a liquid-impermeable sheet on that side of the article which is distal from the wearer in use, said two sheets projecting out beyond the edges of the absorbent pad and being mutually joined around the full periphery of the absorbent pad, wherein the flexible flaps are secured in the casing edge of the liquid-impermeable sheet that projects out from the absorbent pad.

According to a further embodiment, the regions of pressure-sensitive adhesive are provided on the liquid-impermable sheet.

According to a further embodiment, the regions of pressure-sensitive adhesive are provided on the flexible flaps.

A number of advantages are gained when flaps are arranged on an absorbent article in accordance with the present invention, such that the flaps are directed in over the article instead of extending straight out from the side edges of said article, as with the case of the earlier known sanitary napkins.

For example, it enables the articles to be manufactured with negligible wastage of material when cutting-out the articles. Furthermore, the articles can be packaged more readily, since it is not necessary to fold the flaps together.

Furthermore, the flaps are made from separate pieces of material, whose composition and other properties can be freely selected, independently of the material from which the article casing is made. In addition, there is no direct connection between the casing or the absorbent pad of the article and the flaps, thereby interrupting all liquid transport paths therebetween. The joins between the flaps and the remainder of the article thus form a type of leakage barrier.

Further advantages are gained when the flaps are attached on that side of the article which is distal from the wearer in use. For instance, this enables an article to be produced which is shaped according to the curved leg edges of a pair of underpants or like garment. When an article of this kind is placed in a pair of underpants, the leg edges of the underpants are inserted between the flaps and the casing material on the underside of the article, i.e. on that side of the article which is worn distal from the wearer. In use, the article becomes curved in its longitudinal direction, so as to conform to the shape of that part of the wearer's body. This results in tension forces in the flaps, which press the flaps against the casing material on the underside of the article and firmly clamp the leg edges of the underpants between the flaps and the remainder of the article. This "self-locking" of the article to the underpants can obviate the use of separate fastener means, such as adhesive beads or the like. This naturally affords an important advantage, since it enables the article to be handled much more easily, both when positioning the article in a pair of underpants and when removing the used article therefrom. Furthermore, the articles can be manufactured much more simply and more cheaply when it is no longer necessary to provide the articles with attachment adhesive and associated protective tapes.

BRIEF DESCRIPTION OF THE DRAWINGS

An inventive absorbent article will now be described in more detail with reference to exemplifying embodiments thereof and also with reference to the accompanying drawings.

FIG. 1 shows an inventive sanitary napkin from above, as seen from that side of the napkin which faces the wearer in use, with the napkin shown fitted inside a pair of underpants.

FIG. 2 illustrates the napkin of FIG. 1 as seen from that side of the napkin which is distal from the wearer in use.

FIG. 3 is a sectional view of the napkin shown in FIG. 1, taken on the line III—III in said Figure.

DETAILED DESCRIPTION OF THE INVENTION

Figure 4:
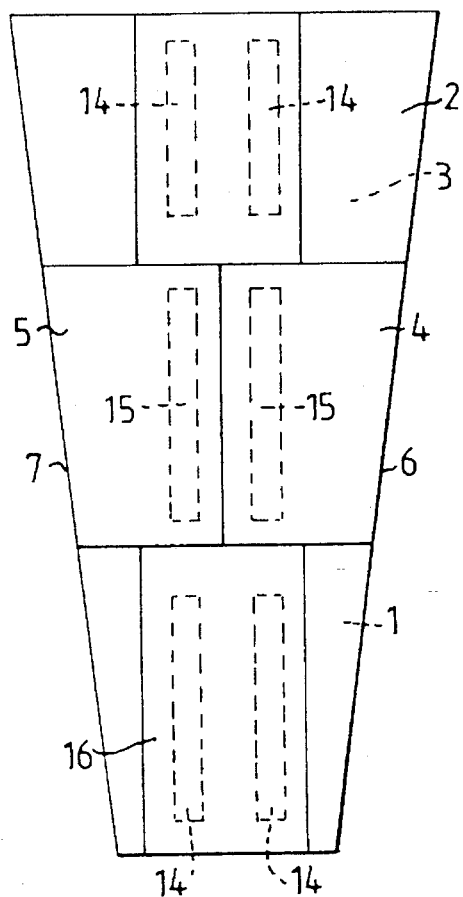
FIG. 4 illustrates a second embodiment of an inventive sanitary napkin, seen from the side of the napkin which is distal from the wearer in use.

The sanitary napkin illustrated in FIGS. 1–3 includes a liquid-permeable casing sheet 1, which is placed on that side of the napkin which faces the wearer in use. The liquid-permeable sheet 1 is suitably made from a nonabsorbent fabric, or from a perforated plastic fill. The sanitary napkin further includes a liquid-impermeable casing sheet 2, for example a plastic fill or a fabric, which has been made hydrophobic on that side of the napkin which is distal from the wearer in use. An absorbent pad 3 is enclosed between the two casing sheets 1, 2. The absorbent pad 3 may comprise one or more layers of absorbent material, such as cellulose fluff, with or without being admixed with so-called superabsorbents. By superabsorbents is meant polymeric materials which are capable of absorbing liquid in amounts corresponding to many times their own weight. Superabsorbents normally have the form of particles, which are admixed with the cellulose fluff, or are applied in separate layers between mutually adjacent fluff layers. Superabsorbents may also be in the form of flakes, granules, films and fibers, as an alternative to a particle form.

Although not shown in the drawings, the absorbent pad 3 may also include other features, such as a liquid dispersing layer and a reinforcing layer made, for instance, of tissue or fabric.

The two casing sheets 1, 2 extend outwardly beyond the edges of the absorbent pad 3, and are mutually joined around the whole of the periphery of the absorbent pad 3, thereby enclosing the absorbent pad between the casing sheets 1, 2. The casing sheets are joined together suitably with the aid of some appropriate, known technique, for example by gluing or heat-welding or ultrasonic-welding.

Two flexible pieces of material or flaps 4, 5 of generally the same length as the two casing sheets are firmly secured along the side edges 6, 7 of the liquid-impermeable sheet sheet 2. The flaps 4, 5 extend inwardly over the liquid-impermeable casing sheet 2, and meet at the longitudinal center line 8 of said sheet. The flaps 4, 5 may, for instance, be made of fabric or plastic film material. In order to facilitate handling of the sanitary napkin when used, the flaps 4, 5 preferably have a certain degree of stiffness, so that they will not wrinkle or fold when applied to a pair of underpants or like garment. Flaps which have a given degree of stiffness will also assist in counteracting compression of the napkin during use.

The sanitary napkin shown in FIGS. 1–3 is placed in the crotch part of a pair of underpants or like garment 9 having elastic leg edges 10, 11, such that the material of the underpants 9 will be located between the liquid-impermable sheet 2 of the napkin and the flexible flaps 4, 5.

The side edges 6, 7 of the casing sheets 1, 2 and the flaps 4, 5 are curved so as to conform as close as possible to the curvature of the leg edges 10, 11 of the underpants 9. Since the width of the crotch part can vary between different makes of underpants or like garment, it is, of course, impossible to provide a sanitary napkin which will fit exactly all types of underpants. When testing 126 pairs of randomly selected ladies' panties of different sizes and models, it was found that the crotch part of a pair of ladies' panties had an average width of 65 mm, measured at the narrowest crotch region. Accordingly, it is appropriate for the sanitary napkin to have approximately this width at its narrowest part. However, it is not necessary for the width and shape of the napkin to correspond totally to the shape and the width of the crotch of the underpants 9. If the crotch is slightly narrower than the distance between the edge joins 12, 13 of the napkin, this will simply mean that the edges 10, 11 of the underpants will not reach fully out to the edge joins 12, 13, and that the sanitary napkin will be able to move laterally to a limited extent when in use. When the crotch is broader than the sanitary napkin, it is necessary to draw or gather the leg edges 10, 11 of the underpants 9 slightly together, so as to enable the napkin to be fitted in the underpants. Any pleats or folds which might form in the crotch of the underpants as a result hereof will lack significance to the function of the napkin and will not have any influence on the wearer's comfort.

When the sanitary napkin is carried in a pair of underpants 9, the napkin will conform to the shape of this part of the wearer's body and is imparted a curved configuration in the longitudinal direction of the napkin. When the napkin is curved longitudinally, tension forces are generated in the flexible flaps 4, 5 on the outside of the underpants 9, causing the flaps 4, 5 to press against the underpants 9 so as to clamp the underpants firmly between the flaps 4, 5 and the liquid-impermeable sheet 2 of the napkin, as shown in FIG. 3. The napkin is hereby held in position in the underpants 9, without needing to use separate securing devices, such as pressure-sensitive adhesive or adhesive tape.

FIG. 4 illustrates a sanitary napkin whose configuration is particularly advantageous from the aspect of manufacture. Similar to the napkin illustrated in FIGS. 1–3, the sanitary napkin of the FIG. 4 embodiment includes an absorbent pad 3 which is enclosed between two casing sheets 1, 2, and flexible flaps 4, 5 which are attached to the liquid-impermeable casing sheet 2 and firmly secured to the longitudinal edges 6, 7 thereof. The liquid-impermeable sheet 2 and the flexible flaps 4, 5 of the sanitary napkin are provided with regions 14, 15 of pressure-sensitive adhesive, for securing the napkin inside a pair of underpants or like garment 9. The adhesive is provided on that side of the flaps 4, 5 which faces towards the liquid-impermeable sheet 2. Prior to use, the adhesive regions 14, 15 are protected by a strip 16 of material treated with a release agent. The protective strip 16 is treated with a release agent on both sides thereof, thereby serving as a protective layer both for the adhesive regions 14 on the liquid-impermeable sheet 2 and for the adhesive regions 15 on the flexible flaps 4, 5.

When the napkin is to be used, the protective strip 16 is removed from the adhesive and the napkin is placed in the crotch of a pair of underpants 9, with the flexible flaps 4, 5 secured to the outside of the underpants. An adhesive or like substance is preferably used to secure the napkin to the underpants, since the flaps 4, 5 of a napkin of the kind illustrated in FIG. 4 are not self-locking in use, as distinct to the flaps of the napkin described with reference to FIGS. 1–3. This is mainly because the edges 6, 7 of the FIG. 4 embodiment are straight instead of curved. Furthermore, the flaps 4, 5 of the napkin according to FIG. 4 only take up a small part of the length of the napkin.

The napkin illustrated in FIG. 4 is particularly well suited for manufacture without material waste. The casing sheets and the material in the flexible flaps and the protective strip which covers the adhesive are all formed from pieces that are taken from endless webs of materials capable of being glued or welded together. The absorbent pad is preferably formed by air-laying the absorbent material form which the pad is made. The finished napkins are clipped or cut to a trapezoidal shape from an endless web. The final cutting stage can be effected without any wastage of material, by arranging the napkins with their broader ends facing in alternate directions.

Figure 5:
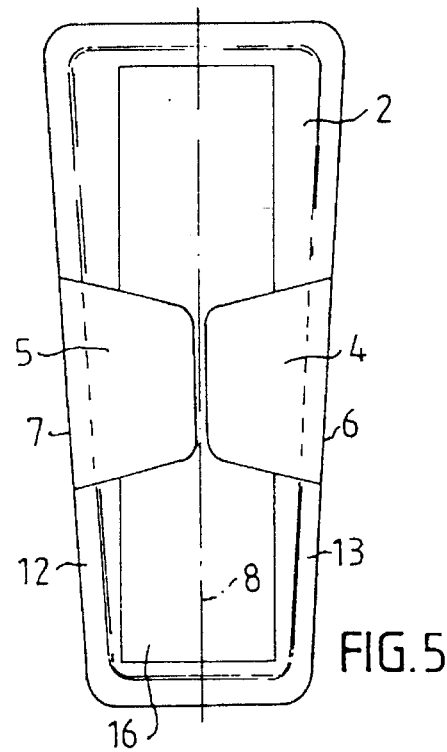
FIG. 5 illustrates a sanitary napkin according to a third embodiment of the invention, seen from the side of the napkin which is distal from the wearer in use, and FIG. 6, finally, is a sectional view of the napkin of FIG. 5 placed within a pair of underpants, in the region of the wearer's crotch.
Figure 6:
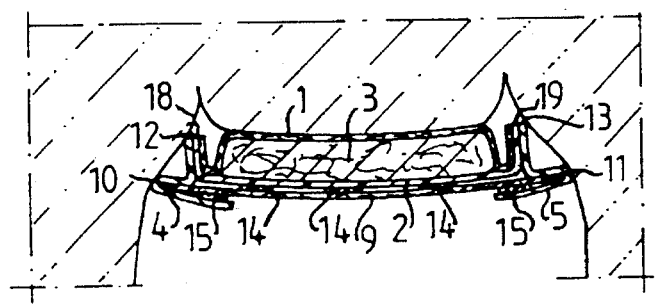

The construction of the sanitary napkin illustrated in FIGS. 5 and 6 is the same as the construction of the napkin illustrated in FIG. 4, and includes an absorbent pad 3 enclosed between two casing sheets 1, 2, and flexible flaps 4, 5 attached to the liquid-impermeable sheet 2 and fastened along the side edges 6, 7 of said sheet. Both the flexible flaps and the liquid-impermeable sheet have regions 14, 15 of pressure-sensitive adhesive, which are covered with a protective layer 16, prior to the napkin being used. However, the napkin illustrated in FIGS. 5 and 6 differs from the napkin illustrated in FIG. 4, in that the longitudinal side edges 6, 7 are not inclined to the same extent in relation to the longitudinal center line 8 of the napkin, and in that the napkin is somewhat narrower than the napkin of the FIG. 4 embodiment. The napkin hereby obtains a slightly different functioning mode.

When a napkin according to the embodiment illustrated in FIGS. 5 and 6 shall be placed within a pair of underpants 9 or like garment, the protective strip 16 is removed so as to first expose the adhesive regions 14, 15. The side-flaps 4, 5 are then unfolded away from the absorbent pad 3. The flaps 4, 5 therewith forcibly raise parts of the edge joins 12, 13 projecting outwardly of the absorbent pad, so as to form uplifted liquid barriers 18, 19 on both sides of the absorbent pad 3. The extension of the liquid barriers 18, 19 in the longitudinal direction of the napkin will, of course, depend on the size of the edge joins 12, 13 connected to a respective side flap 4, 5. That part of the edge joins 12, 13 which can be raised by each flap 4, 5, however, is much longer than the actual join 12, 13 between the flaps 4, 5 and the casing. Consequently, it is possible to obtain effective and efficient upstanding liquid barriers 18, 19 even with relatively small flaps 4, 5. This is, of course, particularly advantageous from the aspect of discretion and also with view to the ease with which the napkin can be handled.

FIG. 6 is a sectional view illustrating how the sanitary napkin is carried in the crotch region of the user. The napkin is secured in the wearer's underpants 9 by means of regions 14 of pressure-sensitive adhesive provided at the end parts of the napkin on the liquid-impermable sheet 2. The flexible flaps 4, 5 are folded around the leg edges 10, 11 of the leg openings of the underpants 9 and are secured to the outside of said underpants. Regions 15 of pressure-sensitive adhesive are also provided on the flaps 4, 5 for this purpose.

Because the absorbent pad 3 of the sanitary napkin is slightly narrower than the crotch part of the underpants 9, the flaps 4, 5 will extend laterally outwards from each long edge of the elongated absorbent pad, prior to folding the flaps 4, 5 around the leg edges 10, 11 of the underpants 9. When the napkin is worn, the elastic devices in the leg edges 10, 11 will exert a given tension force on the napkin, so that the absorbent pad 3 and those parts of the flaps 4, 5 which are located between the leg edges 10, 11 will be stretched in the transverse direction of the napkin. In this way, the major part of the edge joins 12, 13 along the long sides of the absorbent pad 3 will be held raised while the napkin is worn. Such uplifted barriers 18, 19 are particularly effective against leakage of body fluid over the edges of the napkin, and also against the spreading of liquid into the side-flaps 4, 5 of said napkin. Because the liquid-impermeable sheet 2 of the napkin extends out into the upraised casing edges 18, 19, and because the side-flaps 4, 5 are made of separate pieces of material, there is no risk of liquid spreading across the liquid barriers 18, 19. It is possible, and in fact suitable, to produce the flaps 4, 5 from a liquid-permeable material. The flaps 4, 5 are mainly intended to function as means for securing and stretching an absorbent article in a pair of underpants or like garment, and need not have liquid obstructing properties. Thus, by producing the flaps from an air-and-moisture pervious material, it is possible to provide a sanitary napkin which is cooler and more comfortable to wear than earlier known sanitary napkins in which the flaps form liquid-impervious leakage barriers.

Although the invention has been described with reference to sanitary napkins, it will be understood that the invention can be applied equally as well as incontinence guards.

The invention shall not be considered limited to the described and illustrated embodiments thereof. For example, it is possible to vary the shape and the size of the flaps of the article and of the absorbent pad. The flexible flaps need not meet at the centre line of the article, but may overlap one another or may simply extend slightly inwards towards the centre line from each side edge.

Furthermore, the article may be of the kind in which the casing comprises a single sheet of material which is folded and sealed around the absorbent pad.

The means used to secure the article in place in a pair of underpants may be different to those described and illustrated. For example, the article may include friction means or self-gripping tape, or may have pressure-sensitive adhesive provided in patterns other than those illustrated and described.

The outwardly projecting flaps may be produced from any appropriate type of material, which may be elastic, for instance.

I claim:

1. An absorbent article, intended to be worn in the crotch part of a pair of underpants and including: an elongated absorbent pad enclosed in a casing and flexible flaps which are attached to respective long edges of said pad, each said flap being formed of a separate material piece and intended to be folded around leg edges of the underpants in use, so as to protect the underpants against soiling, each flap having an edge part which coincides generally with a corresponding edge part on the article casing; said flaps and said casing being mutually joined within an attachment area located in the mutually coincident edge parts, with the flaps extending inwardly over the absorbent pad on the side of the casing remote from the wearer when the article is in use, and said flaps being foldable along a longitudinal axis inwardly of the attachment area.

2. An article according to claim 1, wherein the long edges have a concave curvature, whereby the article has generally the same shape as the crotch part of a pair of underpants.

3. An article according to claim 1, wherein the flaps extend along the full length of side edges of the article.

4. An article according to claim 1, wherein the casing includes a liquid-permeable sheet on that side of the article which faces the wearer in use, and a liquid-impermeable sheet on that side of the article which is distal from the wearer in use, said two sheets projecting out beyond edges of the absorbent pad and being mutually joined around the full periphery of said absorbent pad; and said flexible flaps being secured to casing edges of the liquid-impermeable sheet projecting out from the absorbent pad.

5. An article according to claim 4, further including regions of pressure-sensitive adhesive arranged on the liquid-impermeable sheet.

6. An article according to claim 5, further including regions of pressure-sensitive adhesive arranged on the flexible flaps.

* * * * *